United States Patent [19]

Bringhurst et al.

[11] Patent Number: Plant 6,579

[45] Date of Patent: Jan. 31, 1989

[54] STRAWBERRY POANT CALLED 'MRAK'

[75] Inventors: Royce S. Bringhurst, Davis; Victor Voth, Santa Ana, both of Calif.

[73] Assignee: Regents of the University of California, Berkeley, Calif.

[21] Appl. No.: 74,439

[22] Filed: Jul. 16, 1987

[51] Int. Cl.[4] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A strong day-neutral type prolific fruiting with good flavor, resistant to Verticillium Wilt and capable of fruiting about three months after planting under satisfactory growing conditions regardless of planting time. The plant is of interest in all situations where 'Hecker' or 'Fern' are grown.

2 Drawing Sheets

DESCRIPTION

This invention relates to a new and distinctive day-neutral type strawberry cultivar designated as 'Mrak' which is the result of a cross between 'Hecker' (U.S. Plant Pat. No. 4,507) and 'Aiko' (U.S. Plant Pat. No. 3,981) made in 1975.

'Mrak' first fruited at the University of California Wolfskill Experimental Orchards near Davis in 1977 where it was selected and designated originally as Cal 75.34-105. It was tested later as advanced selection CN 27.

'Mrak' has been propagated asexually by runners and has been tested at various University of California field stations and facilities and to a very limited extent in a few growers' field under Test Agreement.

In the photographs:

Figure 1:
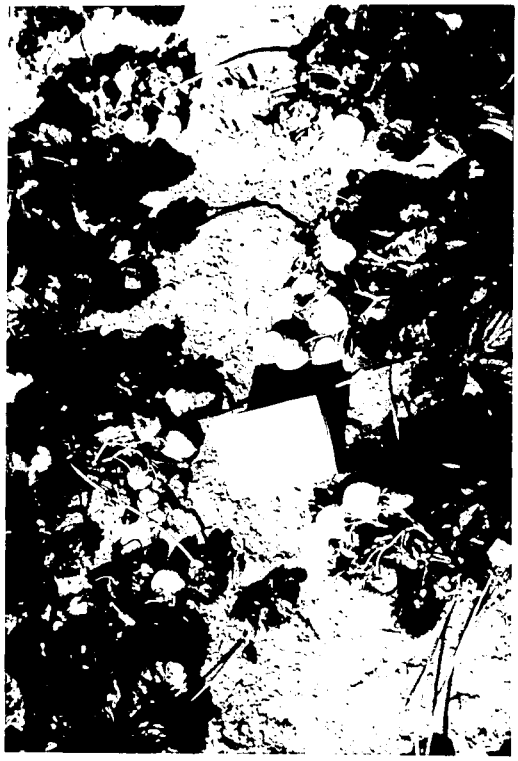
FIG. 1 shows typical growth, flowering and fruiting characteristics of the plant.
Figure 2:
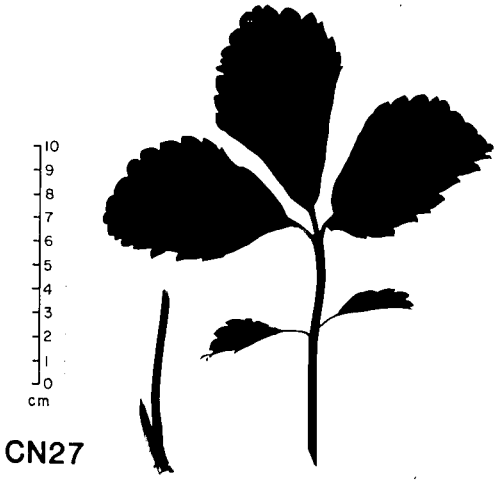
FIG. 2 shows a typical mid-fall mature leaf from a nursery plant.
Figure 3:
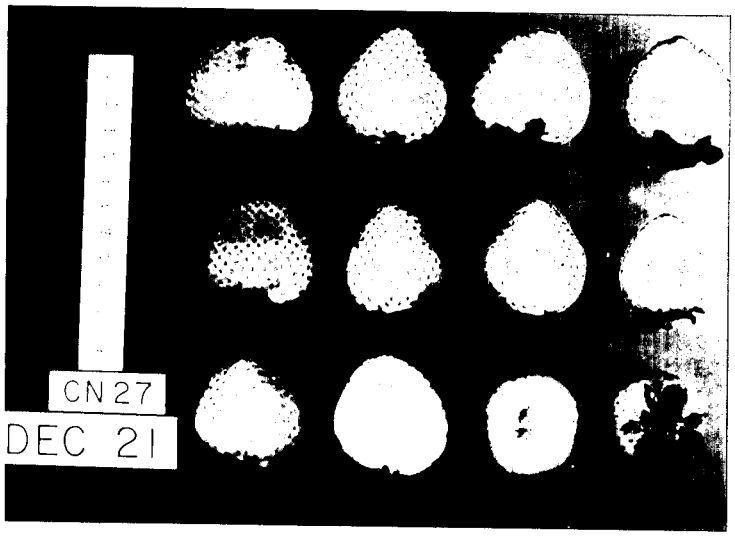
FIG. 3 shows representative early-season fruit with longitudinal and cross-sectional views.

'Mrak' commences fruiting about three months after planting, whether fresh dug or cold storage plants are used, regardless of planting time provided that satisfactory growing conditions prevail. 'Mrak' is at least as strongly day-neutral as 'Brighton' (U.S. Plant Pat. No. 4,489, 'Hecker' and 'Fern' (U.S. Plant Pat. No. 5,267).

Plant and Foliage: 'Mrak' plants are relatively low growing. Leaf color and characteristics from late summer nursery plants of 'Mrak' are compared with those of 'Selva', 'Fern' and 'Hecker' in Table 1:

TABLE 1

| | MRAK | SELVA | FERN | HECKER |
|---|---|---|---|---|
| Color | 2.5 GY 4/3 | 7.5 GY 4/4 | 7.5 GY 4/4 | 2.5 GY 4/3 |
| Shape (length/Width) | 1.26 | 1.20 | 1.10 | 1.13 |
| Base angle of terminal leaflet | 44° | 51° | 58° | 56° |
| Size of terminal leaflet | 77 | 86 | 70 | 76 |
| Serrations of terminal leaflet | 8.7 | 9.8 | 9.3 | 8.0 |
| Petiolule length (MM) | 8.5 | 11.4 | 7.7 | 9.3 |
| Petiole length (MM) | 141 | 161 | 155 | 137 |

TABLE 1-continued

| | MRAK | SELVA | FERN | HECKER |
|---|---|---|---|---|
| Bract leaf position | 74 | 68 | 61 | 64 |

As shown above 'Mrak' leaves are about the same color as those of 'Hecker', darker than 'Selva' or 'Fern' (Munsell Color System — Nickerson Color Fan). Terminal leaflets somewhat elongated and slightly narrow as shown by the length/width measurement and the more acute half blade basal angle compared with 'Selva', 'Fern' and 'Hecker'. 'Mrak' terminal leaflets are about the same size as those of 'Hecker', larger than 'Fern' and smaller than 'Selva' as determined by extracting the square root of the length×width measurements. Leaf serration numbers are greater than for 'Hecker' and less than 'Selva' and 'Fern'. Petiolules (terminal leaflet stems) of 'Mrak' are shorter than those of 'Selva' and 'Hecker' but longer than those of 'Fern'. 'Mrak' plants are small, about the same size as those of 'Hecker' as indicated by petiole length but more recumbent than any of the other day-neutral California cultivars. About 20% of the petioles of 'Mrak' have bract leaves present, located about 74% of the way up the petiole, somewhat higher than the comparison cultivars. Runner production in nursery plants of 'Mrak' is good, only a little less than for 'Selva'.

Isozymes in leaf extracts: 'Mrak' has been characterized for three enzyme systems by starch gel electrophoresis: A. Phophoglucoisomerase (PGI); B. Leucine Amino Peptidase (LAP) and; C. Phosphoglucomutase (PGM). They compare with the other California day-neutral cultivars as follows:

TABLE 2

| | MRAK | SELVA | FERN | HECKER | APTOS & BRIGHTON |
|---|---|---|---|---|---|
| PGI | A1 | A2 | A4 | A1 | A4 |
| LAP | B3 | B3 | B3 | B1 | B3 |
| PGM | C2 | C2 | C2 | C4 | C4 |

'Mrak' can thus be distinguished unambiguously from any of the other California day-neutral cultivars by using the three enzyme systems.

Disease and pest reaction: 'Mrak' is highly resistant to (tolerant of) the virus diseases common in California, including Mild Yellow Edge alone and in complexes.

'Mrak' is quite highly resistant to Verticillium wilt (about equal to 'Hecker'). It is fairly susceptible to common leaf spot (Ramularia) and is less susceptible to two-spotted mite infestations than 'Selva'.

Flowering, fruiting, fruit and production characteristics: 'Mrak' is a strong day-neutral similar in physiological response to 'Fern' or 'Hecker' in that it will flower and fruit anytime, effectively independent of day length. It is earlier than 'Fern' or 'Hecker' under most conditions. Flowers are borne on medium long peduncles that tend to be more outspreading rather than erect in growth habit. The flowers are medium in size with five to six petals and are completely self-fertile with ample pollen throughout the season. Pollination is generally complete with very few malformed fruit. The fruit shape is symmetrical, medium to long conic, with slightly hollow centers. 'Mrak' fruit yield and midseason fruit and quality characteristics are compared with those of 'Selva', 'Fern', 'Hecker' as grown under optimum conditions under the "hill" system in "winter" plantings at the University of California Strawberry Research Facility, Watsonville in Table 3 as follows:

TABLE 3

| | MRAK | SELVA | FERN | HECKER |
|---|---|---|---|---|
| Yield (GR/Plant) | 1389 | 1557 | 1502 | 1556 |
| Size (GR/Fruit) | 18.3 | 25.9 | 22.4 | 16.2 |
| Firmness | 5.2 | 6.8 | 5.4 | 5.3 |
| Color | 7R4/11 | 7R4/11 | 5R3.5/12 | 7.5R4.5/13 |
| Ascorbic Acid | 34.6 | 24.1 | 27.8 | 46.7 |
| Soluble Solids | 8.6 | 8.1 | 7.9 | 7.6 |

Over time, 'Mrak' is capable of yielding about as much fruit as the other day-neutrals. The fruit of 'Mrak' varies considerably in size and averages larger than that of 'Hecker' but smaller than 'Fern' or 'Selva' ('Mrak' is about as firm as 'Fern' or 'Hecker') but less firm than 'Selva' as measured by a penetrometer equipped with a "Hunter Force Gage" and it handles well. The fruit skin color is about the same as that of 'Selva', less red than that of 'Fern' and slightly more red than 'Hecker' (ibid). The finish is bright and attractive. The flesh is about the same color as the skin but less intense with a distinctly lighter ring around the core. The achenes are bright yellow to somewhat reddish, positioned about even with the skin surface. The calyx is small to medium, positioned on a tapered somewhat thick neck. 'Mrak' fruit averages a somewhat higher ascorbic acid content than 'Selva' or 'Fern' but somewhat lower than 'Hecker' as measured by the Loeffler and Porting method (1942, J. Induct. and Engin. Chem. 14:846). Soluble solids averaged slightly higher than those for the comparison cultivars. The flavor of 'Mrak' compares favorably with that of 'Selva' or 'Hecker' but not quite as good as that of 'Fern'. 'Mrak' is recommended for fresh market and processing for commercial plantings and home gardening particularly when "off season" fruiting is desired.

We claim:

1. The new distinct variety of strawberry plant herein described and illustrated and identified by the characteristics enumerated above together with the parts thereof.

* * * * *

UNITED STATES PATENT AND TRADEMARK OFFICE

CERTIFICATE OF CORRECTION

PATENT NO. : PLANT 6,579

DATED : January 31, 1989

INVENTOR(S) : Royce S. Bringhurst and Victor Voth

It is certified that error appears in the above-identified patent and that said Letters Patent is hereby corrected as shown below:

PLEASE AMEND THE TITLE AS FOLLOWS:

DELETE "POANT" AND SUBSTITUTE --PLANT--.

Signed and Sealed this

Twenty-fifth Day of July, 1989

*Attest:*

*Attesting Officer*

DONALD J. QUIGG

*Commissioner of Patents and Trademarks*